United States Patent [19]

Sillard

[11] Patent Number: 5,057,017
[45] Date of Patent: Oct. 15, 1991

[54] FIXED REMOVABLE DENTAL IMPLANT SYSTEM

[76] Inventor: Rannar Sillard, 206 Madison Ave., Lakewood, N.J. 08701

[21] Appl. No.: 516,298

[22] Filed: Apr. 30, 1990

Related U.S. Application Data

[63] Continuation-in-part of Ser. No. 314,779, Feb. 24, 1989, Pat. No. 4,931,016.

[51] Int. Cl.$^5$ .............................................. A61C 13/01
[52] U.S. Cl. .................................... 433/172; 433/173; 433/174; 433/167
[58] Field of Search ............... 433/167, 171, 172, 173, 433/174, 175, 176, 199.1, 71; 219/69.15; 29/160.6; 164/DIG. 4

[56] References Cited

U.S. PATENT DOCUMENTS

| | | | |
|---|---|---|---|
| 3,748,739 | 7/1973 | Thibert | 433/173 |
| 4,085,506 | 4/1978 | Lew | 433/172 |
| 4,363,627 | 12/1982 | Windeler | 433/167 |
| 4,767,328 | 8/1988 | Branemark | 433/173 |
| 4,784,608 | 11/1988 | Mays | 433/173 |

Primary Examiner—Cary E. O'Connor
Attorney, Agent, or Firm—Clifford G. Frayne

[57] ABSTRACT

A fixed, removable dental implant having a precision cast support structure secured to the alveolar bone and a female supra structure conforming in shape to the precision cast support bar removably mounted and secured to the precision cast support bar, the supra structure having the acrylic prosthesis secured thereto, the precision cast support bar and female supra structure having conforming configurations achieved by electrical erosion methods to provide the patient with the confidence and security of a fixed dental prosthesis yet permitting the patient to remove the supra structure and acrylic prosthesis for cleaning without the necessity of a dental visit.

4 Claims, 4 Drawing Sheets

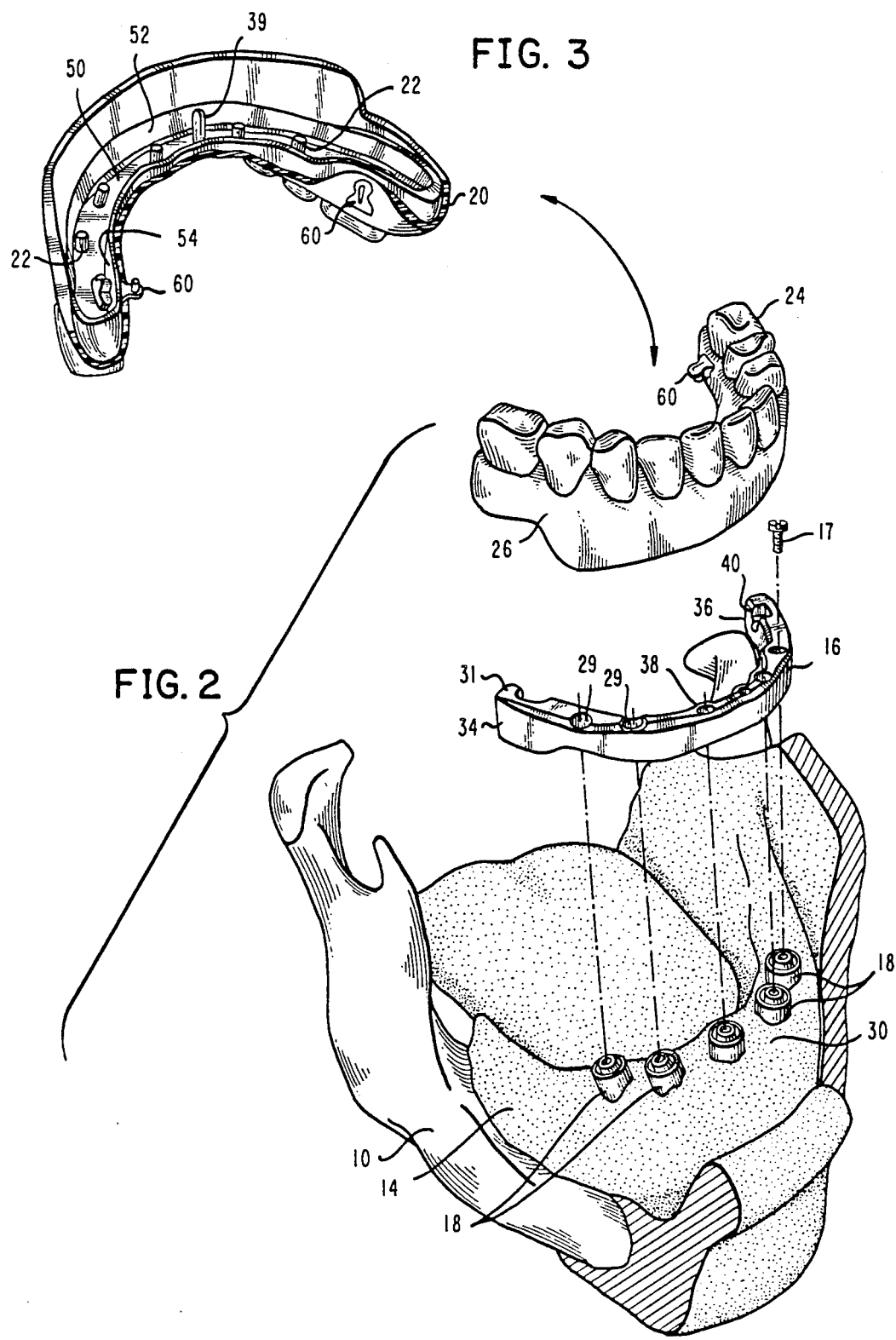

FIXED REMOVABLE DENTAL IMPLANT SYSTEM

This is a continuation in part of U.S. application Ser. Nos. 07/314,779, filed 2/24/89, now U.S. Pat. No. 4,931,016.

FIELD OF INVENTION

The present invention relates to a device for securing a plurality of teeth by means of a plurality of attachment elements to the alveolar bone and, in particular, relates to a device and process for making such device which provides for a removably secured dental implant prosthesis which is firmly secured in place yet removable by the patient for easy cleaning and which provides an aesthetic appearance.

In the area of dental prosthetics, there have been primarily two major types of dental implant prosthetics which have been in use. The first, commonly known as the over denture, provides for a support structure to be implanted in the alveolar bone which support structure extends above the gum line and permits the patient to snap fit the denture in place. This type of construction permits the patient to remove the denture himself and clean the denture and the gum area. The drawback of an over denture is that it does not normally provide sufficient stability under all eating or chewing conditions.

The second type of prosthesis in wide use is that of the fixed prosthesis. Again, a support structure is anchored in the alveolar bone, the support structure extending above the gum line and the prosthesis being permanently secured through the support structure into the bone. This type of denture normally provides a more stable denture for the patient, but aesthetic and hygiene problems arise in that the denture can only be removed by a dentist to permit cleaning of the area under the prosthesis and proximate to the support structure.

U.S. Pat. No. 4,767,328 to Branemark discloses a device for providing such a permanent or fixed prosthesis.

Further, U.S. Pat. No. 3,748,739 to Thibert, U.S. Pat. No. 4,741,698 to Andrews, U.S. Pat. No. 3,641,671 to Roberts, U.S. Pat. No. 4,085,506 to Lew, U.S. Pat. No. 3,514,858 to Silverman, all disclose versions of permanent or fixed implants. U.S. Pat. No. 4,062,119 to Linkow discloses an implant system for use with removable over dentures.

The need therefore exists for a prosthesis which provides the long term stability to the patient together with aesthetic appearances yet which will permit the patient to remove the prosthesis for cleaning not only the prosthesis, but the gum area surrounding the support structure in order to prevent hygiene problems.

Applicant's device is directed towards the solution of this problem by providing for a support structure which is secured to the alveolar bone and which permits the prosthesis to be swivel locked or snap locked in place to this support structure with either a swivel latch or clip, the key to the stability being the exact fit of the support structure implanted in the bone to the supra structure to which the prosthesis is mounted, this fit being accomplished by an electrical erosion system eliminating the need for soldering or milling. This continuation in part addresses itself to the range of parameters associated with applicant's prior application

OBJECTS OF THE INVENTION

It is an object of the present invention to provide for a dental implant prosthesis which provides a stable support structure to which the prosthesis can be removably secured.

It is a further object of the present invention to provide for a dental implant prosthesis which can be removably secured by the patient for hygienic cleaning.

It is a still further object of the present invention to provide for a dental implant prosthesis which when in the secured position, is locked in place and provides the advantages of a fixed denture or prosthesis.

It is a still further object of the present invention to provide for a dental implant prosthesis which makes it easier to position the implant without compromising aesthetics.

It is a still further object of the present invention to provide for a dental implant prosthesis in which the female supra structure housing is precision-fitted to the male support structure and locked in place in order to provide for the stability equivalent of a fixed denture.

SUMMARY OF THE INVENTION

A fixed removable dental implant prosthesis in which a support structure in the form of a precision cast bar is secured to the alveolar bone, and a female supra structure conforming to the shape of the precision cast bar and having mounted thereon the prosthesis, is removably secured to the precision cast bar by means of a locking mechanism or the like, operable by the patient. The stability and precision fit is achieved by the erosion of the female supra structure by means of electrical current as the female supra structure is fitted over the precision cast male bar in a dilecticum mineral oil pool under the influence of electrical current.

BRIEF DESCRIPTION OF THE DRAWINGS

The objects and advantages of the invention as well as other objects and advantages will become evident upon consideration of the drawings where:

FIG. 2 is an exploded perspective view of the fixed removable implant system;

FIG. 3 is a bottom perspective view of the supra structure;

DETAILED DESCRIPTION OF THE DRAWINGS

Figure 1:
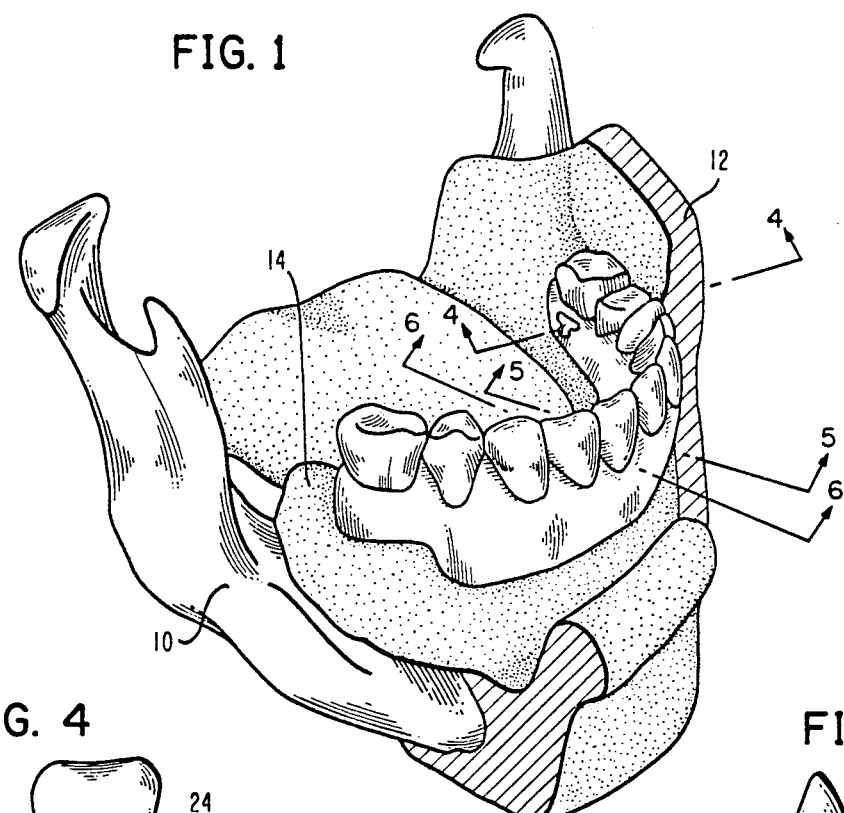
FIG. 1 is a perspective view of the lower jaw with the fixed removable implant system.

Referring to FIG. 1, there is shown a perspective view of the fixed removable implant which is the subject matter of the present invention. In FIG. 1, the implant is shown on an impression model of a patient's mouth in which there is shown the alveolar bone 10 disposed within the jaw 12 with the upper portion of the jaw defined by the gum line 14.

FIG. 2 provides an exploded view of the fixed removable implant and a better understanding of the component elements. A support structure 16 comprising a precision cast bar is anchored in the alveolar bone 10 by means of a plurality of screws 17 which extend downwardly from the precision cast support structure 16, through implant pins or abutments 18 and into the alveolar bone 10. Screws or securing means 17 are recessed in precision cast support structure 16 such that supra structure 20, having a plurality of internally depending detents 22 fit within the recesses of the precision cast support structure 16. In final form, the prosthesis comprising the acrylic teeth 24 and labial flare 26 are secured to the supra structure 20 which is swivel locked onto the precision cast support structure 16 as described hereafter.

The construction of the precision support bar 16 is accomplished from an impression which is made of the patient's mouth, which impression is shown in FIGS. 1 and 2, and which will be described hereafter. The completed precision support structure 16 is mounted to the alveolar bone 10 by means of a plurality of alloy screws 17 which pass through openings 29 on the top of the precision cast support structure 16. Screw 17 are contained within abutments 18 and are secured to the alveolar bone 10. This construction provides a gap or space 30 between precision cast support structure 16 and the upper gum line 14. The precision cast support structure 16 has a substantially flat top surface 31 and tapered sidewalls 34 and 36. The buccal and lingual tapered sidewalls 34 and 36, respectively, are tapered from 0° to 10° from the vertical to aid in the fabrication process as will be described hereafter. It should also be noted that when positioned in place, securing screws 17 are recessed below the top surface 31 of precision cast support structure 16. In this configuration, precision support structure 16 would be permanently implanted in the patient's mouth and could only be removed with a dental procedure. In the fabrication process, precision cast support structure 16 would be secured in a similar manner to a mold of the patient's mouth in order to fabricate the female supra structure 20 for fitting with precision cast support structure 16.

Figure 2A:
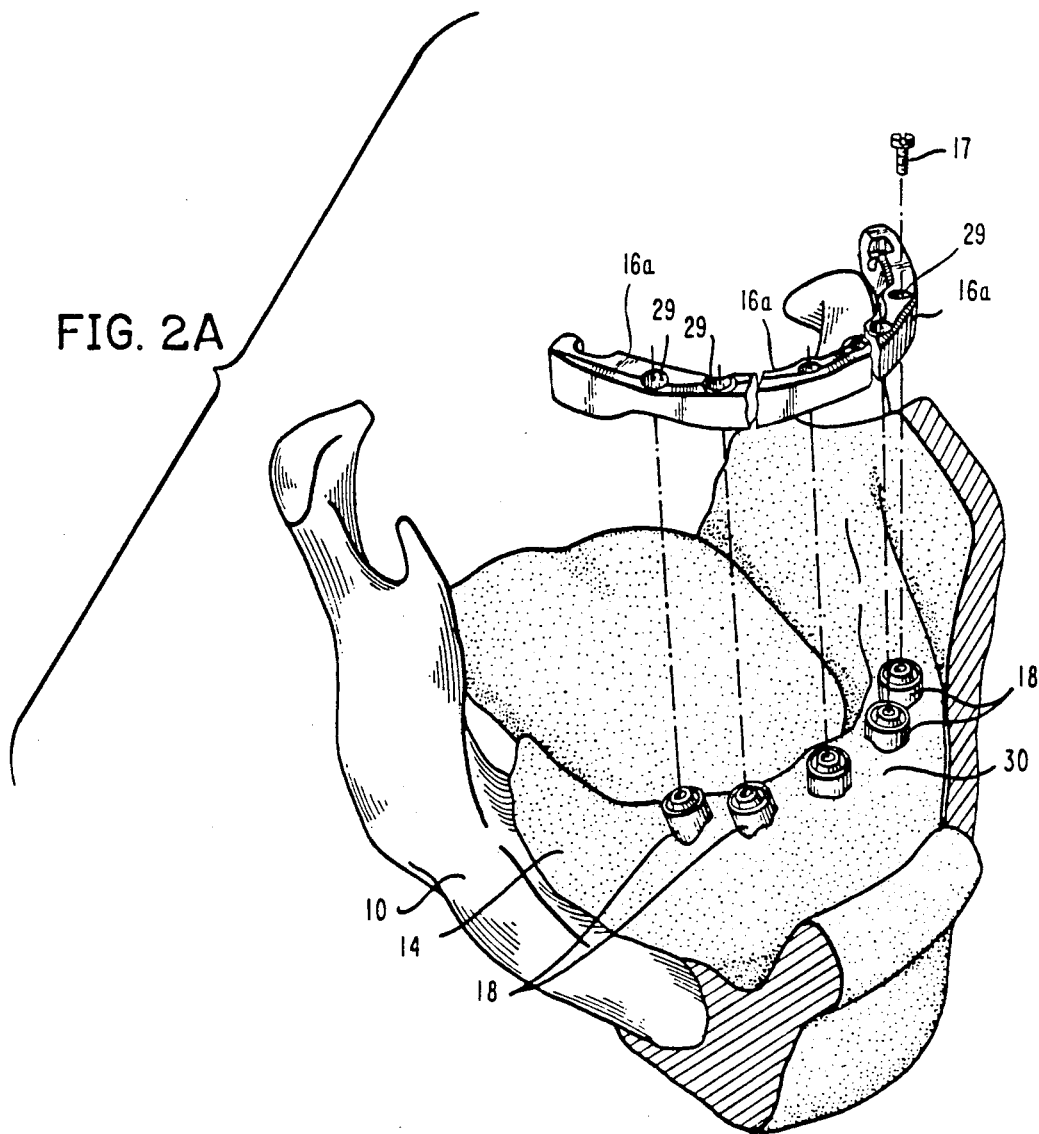
FIG. 2A is a perspective view of a second embodiment of the support bar.
Figure 7:
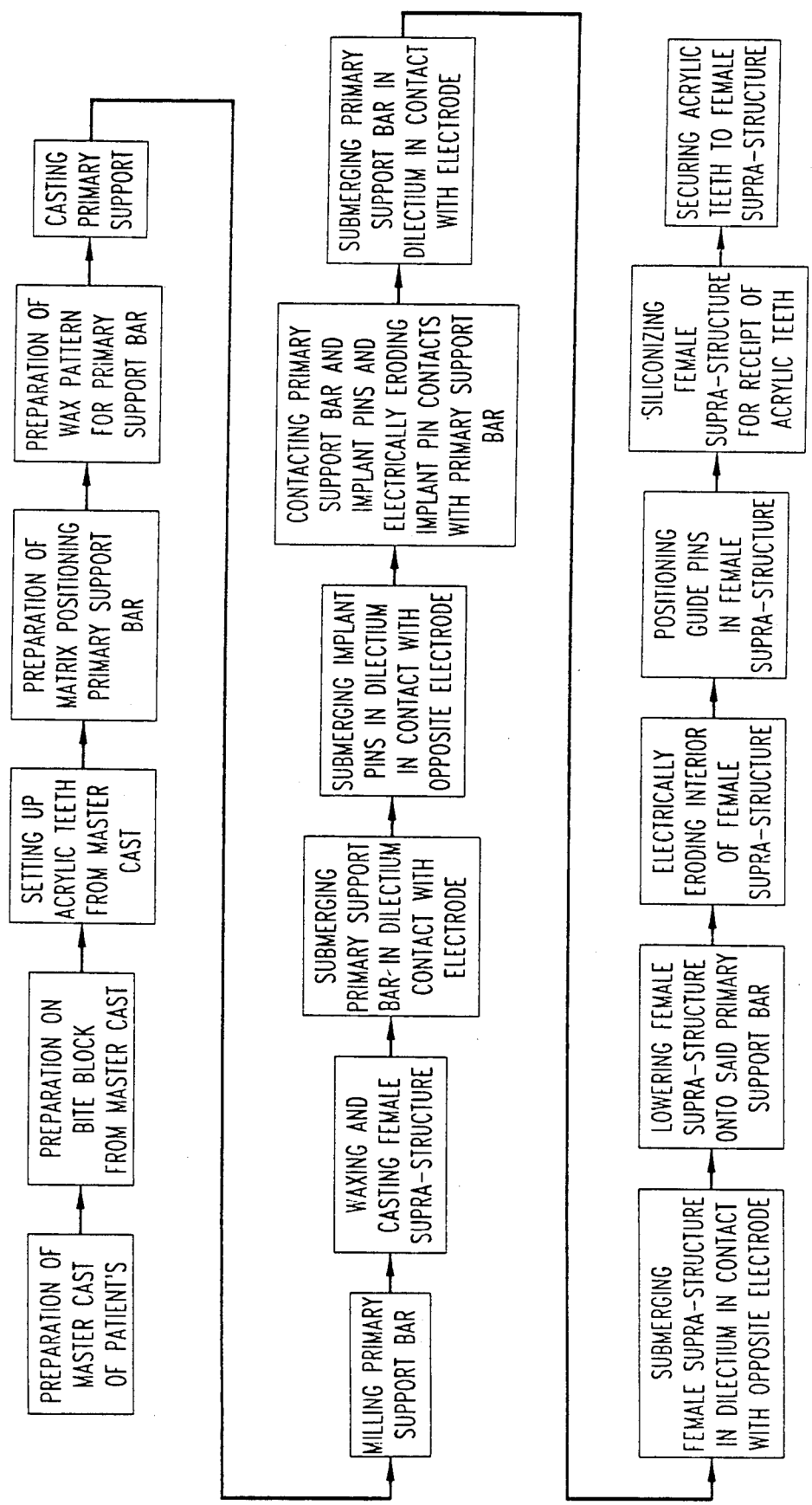
FIG. 7 is a schematic diagram of the process for fabricating the fixed removable implant.

FIG. 2A illustrates a second embodiment of support bar identified as 16A. In this configuration, support bar 16A is discontinuous as opposed to being of single piece construction. The sidewall taper and manner of fabrication are identical to the first single piece embodiment; however, the parameters of the patient's mouth sometimes require a support bar 16 fabricated in sections as shown in the second embodiment.

Figure 6:
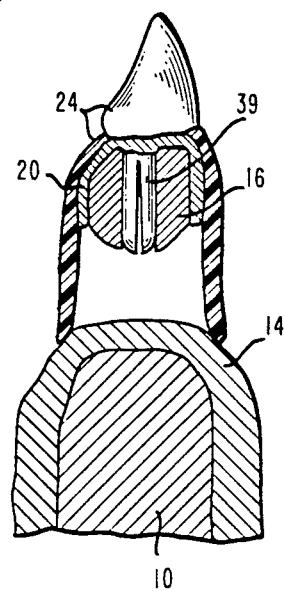
FIG. 6 is a side elevational cutaway view along plane 6—6 detailing the supra structure, support bar and guide pins.

Precision cast support structure 16 contains at least one aperture 38 passing therethrough, in a vertical plane, for the receipt of a guide post 39, see FIGS. 3 and 6, which depends downwardly from female supra structure 20 as described hereafter. This aids in alignment of the female supra structure with the precision cast support structure.

Precision cast support structure 16 may contain two indents 40 normally located proximate to the arcuate ends of precision cast support structure 16 and on the interior buccal taper of precision cast support structure 16. These indents cooperate, as described hereafter, with the female supra structure 10 and the locking mechanism to be described hereafter, in order to secure the female supra structure and prosthesis to precision cast support structure 16.

Referring to FIG. 3, there is shown a bottom perspective view of female supra structure 20. Female supra structure 20 is arcuate in shape and as a result of the fabrication process, is coincidental with the shape of precision cast support structure 16, thus having a substantially flat top surface 50 and tapered sidewalls interior 52 and 54 to coincide with the tapered sidewalls of precision cast support structure 16. Female supra structure 20 has at least one guide post 39 for cooperation with aperture 38 in precision cast support structure 16.

Female supra structure 20 also has formed in its flat upper surface 50, a plurality of detents 22. Detents 22 are formed during the fabrication process with precision cast support structure 16, detents 22 being formed during the fabrication process and coinciding with the indents 29 in the top of precision cast support structure 16 which indents represent the recessed areas for screws 17.

Female supra structure 20 may also have positioned on its interior sidewall, proximate to its arcuate ends, indent 60 for the accommodation of a locking mechanism which cooperates with female supra structure 20 and precision cast support structure 16 to secure the dental implant in place. The acrylic teeth or prosthesis 24 is formed in the normal manner from the patient's impressions. The acrylic teeth or prosthesis 24 is then affixed to female supra structure 20 which, in turn, by means of a swivel lock mechanism, is firmly secured to the implanted precision cast support structure 16 providing the patient with a implant as stable as a permanently affixed implant but which permits the patient to manipulate the swivel lock mechanism to remove the prosthesis 24 together with the female supra structure 20 for cleaning and to permit the patient to clean the precision cast support structure 16, upper gum area 14, and interstitial space 30 between precision cast support structure 16 and the upper surface of the gum 14.

The stability of the fixed removable implant disclosed herein is accomplished through the precision fabrication of the precision cast support structure 16 and the female supra structure 20.

The precision fabrication by means of an erosion process as described hereafter contributes to the stability of the prosthesis and can obviate the need for detents 40 which would accommodate the locking mechanism. The support bar 16 or 16A and female supra structure 20 would be secured by frictional engagement for normal use, but disengaged by the wearer for cleaning.

Figure 4:
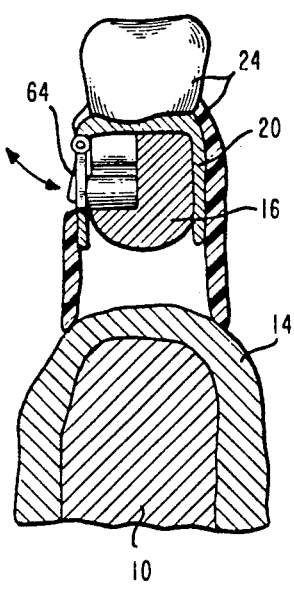
FIG. 4 is a side elevational cutaway view along plane 4—4 of FIG. 1 detailing the lock mechanism.
Figure 5:
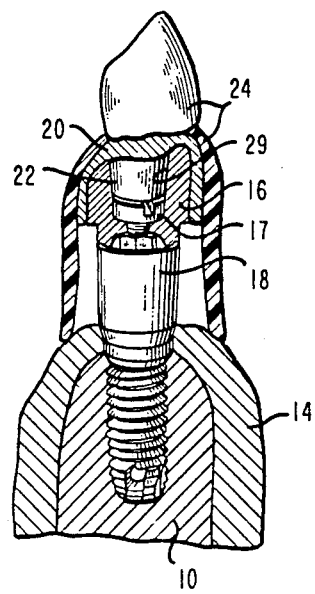
FIG. 5 is a side elevational cutaway view along plane 5—5 of FIG. 1 detailing the supra structure and support bar.

Referring to FIGS. 4, 5 and 6, there is shown sectional views along respective planes 4—4, 5—5 and 6—6 of FIG. 1. These sectional views show the precision cast bar 16 with supra structure 20 mounted thereon. In each configuration, the acrylic teeth prosthesis 24 is mounted to the female supra structure.

FIG. 4 is a sectional view along plane 4—4 of FIG. 1 and which shows the cooperation of the locking mechanism 64 with cooperative recessed indent 60 in female supra structure 20 and precision cast bar 16. The particular locking mechanism shown in FIG. 4 is that of a swivel lock which maintains the female supra structure 20 and acrylic prosthesis 24 in secure, locking contact with precision cast bar 16.

FIG. 5, which is a sectional view along plane 5—5 as shown in FIG. 1, shows the manner in which the precision cast bar is secured to the alveolar bone 10. The abutment 18 has a downwardly extending exteriorly threaded screw which is mounted by means of dental surgery, in the alveolar bone 10. The abutment 18 has an interior threaded recess for receipt of securing screw 17 which secures precision cast bar 16 to abutment 18. When the female supra structure 20 is fitted to the precision cast bar 16, the detents 22 on the interior upper surface 50 of the female supra structure 20 fit within the recess 29 in precision cast bar 16 to aid in maintaining the stability of the female supra structure and acrylic teeth in contact with precision cast bar 16.

FIG. 6 is a sectional view along plane 6—6 in FIG. 1 which shows one of the plurality of guide pins 39 which is utilized for alignment of the female supra structure 20 with the precision cast bar 16. Guide pin 39 depends from the internal upper surface 50 of female supra structure 20 and is in alignment with and fits within aperture 38 in precision case bar 16. In the embodiment shown, a single guide pin is utilized; however, multiple guide pins may be utilized.

Thus far, the structure of the fixed removable implant has been disclosed with respect to its implantation and positioning within the patient's mouth. The method of manufacture of the fixed removable implant is important in obtaining the stability required by the patient, yet still permitting the patient the ability to remove the implant for cleaning. The process of manufacture is set forth hereafter.

A mold is made from the impression of the patient's mouth and the precision cast support structure 16 is cast to conform to the configuration of the patient's mouth. The precision cast support structure 16 is cast in a vacuum which results in metal to metal fusion and one-piece solid construction requiring no soldering or milling.

The precision cast bar 16 is then placed on a mold of the patient's mouth as shown in FIGS. 1 and 2 and the apertures for securing screws 17 and for the guide post are cut in precision cast support structure 16. Precision cast support structure 16 is then mounted with securing screws 17 and abutment 18 on the mold in the configuration in which it will be placed in the patient's mouth.

The female supra structure 20 is fabricated from a wax refractory model of precision cast support structure 16. Precision support structure 16 mounted on the mold of the patient's mouth is then secured within an electrical erosion machine. Machines of this type have been used in the past to fabricate certain support structures for a dental implant, but the system has never been adapted for the coincidental fitting of a female supra structure 20 and precision cast support structure 16 as disclosed herein in order to provide for a fixed removable dental implant.

The devices utilized are normally referred to as EDM or Electrode Discharge Methods which utilize low voltage and low amperage under reversing polarity.

The precision cast support structure 16 secured to the working model of the patient's mouth is connected to a first electrode and the supra structure is connected to a second electrode. The precision cast support structure 16 is submerged in mineral oil or dilectium and aligned with the female supra structure 20. The female supra structure 20 is then gradually lowered into contact with the precision cast support structure 16 with current flowing through the electrodes and hence through the female supra structure 20 and precision cast support structure 16. The gradual lowering and contact of the female supra structure with precision cast support structure 16 under the influence of the electrical current gradually erodes the interior cavity of the female supra structure so that it conforms exactly to the exterior configuration of precision cast support structure 16. In this manner, detents 22 in the interior upper surface 50 of female supra structure 20 are formed as a result of the contact with indents 29 in upper surface 31 of precision cast support structure 16.

When the erosion is completed, female supra structure 20 conforms exactly to the configuration of precision cast support structure 16.

At that point, optional indents are formed in the arcuate ends of both female supra structure 20 and precision cast support structure 16 for the inclusion of a swivel lock mechanism 64 to removably secure the female supra structure 20 to precision cast support structure 16.

At the conclusion of this process, the female supra structure 20 and precision cast support structure 16 are polished and the acrylic prosthesis 24 would be secured to female supra structure 20. The securing of the prosthesis 24 to female supra structure 20 does not interfere with the indents 60 for the swivel lock mechanism and the labial flange 26 of prosthesis 24 can be adjusted or fabricated for aesthetic purposes.

Dental procedures would then provide for the implantation of precision cast support structure 16 in the patient's mouth secured to the alveolar bone 10. The prosthesis, secured to the female supra structure 20, is then positioned on precision cast support structure 16 by means of guide rod 39 and the alignment of detents 22 with indents 29 in precision cast support structure 16. The swivel lock mechanism 64 secured to the female supra structure 20 is then switched to the locking position which engages the indents 60 in precision cast support structure 16 to lock the prosthesis in a firm, secure and stable position within the patient's mouth.

The precision fitting by means of erosion of female supra structure 20 to precision cast support structure 16 provides a stable implant equal to that of a fixed prosthesis, yet permits the patient to disengage the acrylic prosthesis 24 and female supra structure 20 to remove same for cleaning and to permit cleaning of the area surrounding the precision cast support structure 16. An optional locking mechanism may further contribute to the stability of the prosthesis.

The process for installing the fixed, removable implant involves the services of the patient's dentist, an oral surgeon and the laboratory in preparing the fixed, removable implant. The patient's dentist is responsible for obtaining the necessary impressions of the patient's mouth and it is the oral surgeon who will actually install the primary bar supports or abutments 18 into the alveolar bone 10. What follows is the necessary steps required in order to fabricate the fixed, removable implant for the patient.

From the impressions made by the patient's dentist, a final model or master cast is prepared and alloy screw 17 and spacers or abutments 18 are positioned on the final master cast in the same positions as if they were being implanted in the patient's mouth. The replacement teeth are set up and fit in cooperation with the patient's dentist. Once the aesthetics and the fitting of the teeth are accomplished, the master cast is impressed into a silicone wall or matrix to identify the exact location for the precision support structure 16.

The precision support structure 16 is cast using the wax reduction method in a box type flask for uniform expansion. Their burnout phase is accomplished in a burnout furnace having four sided heating elements for uniform heat distribution. The casting is done in a vacuum followed by an atmosphere of 95% argon and 5% hydrogen and by using the gas vacuum principal metal to metal fusion of the alloy and casting gold is accomplished. The gold utilized must be high fusing palladium gold with a melting point of approximately 1,145° F. After casting, the material is allowed to cool under the gas mixture in the casting machine. The precision support structure 16 is then finished and milled in to proper form to provide for an area for the attachment of the securing mechanism as described hereafter. The precision cast support structure 16 is then prepared for silicone duplication with the refractory model being poured in high heat phosphate investment.

The female supra structure 20 is waxed and cast in the same manner as the primary bar. The female supra structure is fitted to approximately 95% of the final fit over the precision cast support structure 16.

The precision cast support structure 16 is then fit to the female supra structure 20 using an erosion system by connecting the precision cast support structure 16 to either a positive or negative electrode and the female supra structure to the opposite electrode while submerged in a mineral oil bath. The precision cast support structure 16 and female supra structure 20 are then brought into gradual contact with each other such that the erosion occurs with respect to the female supra structure 20 such that it fits securely to precision cast support structure 16. Guide pins 39 are plasma welded to the female supra structure 20 to serve as guides for the melding of the precision cast support structure 16 and the female supra structure 20. The abutments 18 may also be fitted to primary cast support structure 16 in the same manner with the precision cast support structure 16 connected to either a positive or negative electrode and the abutments 18 connected to the opposing electrode. This method will ensure a proper fit between the abutments 18 and precision cast support bar 16 once abutments 18 have been secured in the alveolar bone.

The securing mechanism if desired or required is then eroded while the female supra structure 20 and the precision cast support structure 16 are secured together. This again is accomplished in a mineral oil bath.

A swivel latch or elasto clip securing means 64 is then secured to the female supra structure 20 which interlocks with the precision cast support structure 16 to hold the prosthesis securely in place. The female supra structure 20 is then siliconized to prepare it for the receipt of the acrylic teeth. It should again be pointed out that the separate securing mechanism may or may not be employed. The erosion of the fabrication of support bar 16 or 16A and female supra structure 20 can provide for the frictional engagement and stability of the prosthesis and still provide removability without the need for the securing mechanism in the nature of a swivel latch or the like.

The fixed removable implant system as disclosed herein, permits the design and construction of a fixed removable dental implant which when placed in the patient's mouth, provides the patient with the confidence and security of a permanently fixed implant, but allows the patient the convenience of the ability to remove the supra structure and acrylic prosthesis attached thereto for cleaning and to permit the patient to clean the area of the gum and jaw proximate to the precision cast support bar. Not only does the patient have the confidence and security of an implant which is aesthetically pleasing and which permits the patient to eat in a normal manner, but, the patient also has the convenience of the removability of the acrylic prosthesis for cleaning without the necessity of frequent and sometimes expensive dental appointments.

While the present invention has been described in connection with the exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

I claim:

1. A process for the fabrication of a fixed removable dental implant having a primary support bar, a female supra structure secured to said primary support bar and acrylic teeth or prosthesis secured to said female supra structure comprising:
   a. preparing a master cast of the patient's mouth;
   b. preparing bite blocks with tracings and setting up said acrylic teeth for fit and aesthetics;
   c. preparing a silicone matrix for the positioning of said primary support bar;
   d. preparing a wax pattern of said primary support bar;
   e. casting said primary support bar;
   f. milling said primary support bar for proper shape;
   g. waxing and casting said female supra structure;
   h. connecting said primary support bar to an electrode and submersing said primary support bar in a mineral oil or dilectium bath;
   i. connecting said implant pins to an opposing electrode and submersing said implant pins in said mineral oil or dilectium bath;
   j. gradually contacting said implant pins and said primary support bar, electrically eroding the interior of said primary support bar to conform to the exterior configuration of said implant pins;
   k. connecting said primary support bar to an electrode and submersing said primary support bar in a mineral oil or dilectium bath;
   l. connecting said female supra structure to an opposing electrode and submersing said female supra structure in said mineral oil or dilectium bath;
   m. gradually lowering said female supra structure onto said primary support bar, electrically eroding the interior of said female supra structure to conform to the exterior configuration of said primary support bar;
   n. plasma welding guide pins to said female supra structure for path insertion of said female supra structure onto said primary support bar;
   o. siliconizing the female supra structure for receipt of said acrylic teeth;
   p. securing said acrylic teeth to said female supra structure.

2. A process in accordance with claim 1 wherein said casting and milling of said primary support bar results in a sidewall taper in the range of 0° to 10°.

3. A process in accordance with claim 1 wherein said electrical erosion of said female supra structure to said primary support bar results in the interior of said female support supra structure conforming to the exterior configuration of said primary support bar.

4. A process in accordance with claim 1 wherein a complimentary indent is eroded in said female supra structure and said primary support bar accommodating a locking means, removably securing said female supra structure and said acrylic teeth to said primary support bar.

* * * * *